US011246276B2

(12) United States Patent
Shin et al.

(10) Patent No.: US 11,246,276 B2
(45) Date of Patent: Feb. 15, 2022

(54) POWDERY MILDEW RESISTANCE MARKER FOR WINTER SQUASH PLANTS, POWDERY MILDEW RESISTANT WINTER SQUASH PLANT, METHOD FOR PRODUCING POWDERY MILDEW RESISTANT WINTER SQUASH PLANT USING THE SAME, AND METHOD FOR IMPARTING POWDERY MILDEW RESISTANCE TO WINTER SQUASH PLANT

(71) Applicant: Takii & Company Limited, Kyoto (JP)

(72) Inventors: Hisanori Shin, Kyoto (JP); Keitaro Sakaguchi, Kyoto (JP); Hiroshi Asami, Kyoto (JP); Shintaro Matsui, Kyoto (JP); Akihito Kano, Kyoto (JP); Sayaka Kodani, Kyoto (JP)

(73) Assignee: TAKII & COMPANY LIMITED, Kyoto (JP)

( * ) Notice: Subject to any disclaimer, the term of this patent is extended or adjusted under 35 U.S.C. 154(b) by 0 days.

(21) Appl. No.: 16/634,744

(22) PCT Filed: Jul. 31, 2018

(86) PCT No.: PCT/JP2018/028710
§ 371 (c)(1),
(2) Date: Jan. 28, 2020

(87) PCT Pub. No.: WO2019/026924
PCT Pub. Date: Feb. 7, 2019

(65) Prior Publication Data
US 2020/0205362 A1 Jul. 2, 2020

(30) Foreign Application Priority Data

Jul. 31, 2017 (JP) .............................. JP2017-147647

(51) Int. Cl.
*A01H 1/04* (2006.01)
*A01H 6/34* (2018.01)

(52) U.S. Cl.
CPC .............. *A01H 1/04* (2013.01); *A01H 6/348* (2018.05)

(58) Field of Classification Search
CPC . A01H 5/08; A01H 6/348; A01H 1/04; A01H 1/045; A01H 1/1255
See application file for complete search history.

(56) References Cited

U.S. PATENT DOCUMENTS

| 2008/0307540 A1 | 12/2008 | Hofstede et al. |
| 2009/0172836 A1 | 7/2009 | Mazereeuw et al. |
| 2018/0325057 A1 | 11/2018 | Kosugi et al. |
| 2020/0205362 A1 | 7/2020 | Shin et al. |

FOREIGN PATENT DOCUMENTS

| CN | 104498484 A | 4/2015 |
| GN | 101351116 A | 1/2009 |
| GN | 101495639 A | 7/2009 |
| GN | 104560983 A | 4/2015 |
| JP | 2009-542198 A | 12/2009 |
| JP | 2017-086016 A | 5/2017 |
| JP | 6306252 B1 | 4/2018 |
| NL | 2009231 A | 11/2012 |

OTHER PUBLICATIONS

Lawson, Vincent, "Evaluation of Winter Squash Cultivars with Resistance to Powdery Mildew" (2006). Iowa State Research Farm Progress Reports. 1073. http://lib.dr.iastate.edu/farms_reports/1073 (Year: 2006).*
Robinson, R. W., and N. Y. Gneva. "Squash and pumpkin." Horticultural Sciences Department, New York, State Agricultural Experiment Station, Geneva, New York 100 (1995): 250. (Year: 1995).*
Ferriol, María, and Belén Picó. "Pumpkin and winter squash." Vegetables I. Springer, New York, NY, 2008. 317-349. (Year: 2008).*
Zhang, Q. I., Enda Yu, and Andy Medina. "Development of advanced interspecific-bridge lines among Cucurbita pepo, C. maxima, and C. moschata." HortScience 47.4 (2012): 452-458. (Year: 2012).*
Holdsworth, William L., et al. "Cultivar-based introgression mapping reveals wild species-derived Pm-0, the major powdery mildew resistance locus in squash." PloS one 11.12 (2016): e0167715. (Year: 2016).*
Extended European Search Report issued in corresponding European Patent Application No. 18840171.5 dated Feb. 5, 2021.
Database Genbank [Online] Jun. 7, 2016 (Jun. 7, 2016), Anonymous: "Predicted: Cucumis melo uncharacterized LOC103484720 (LOC103484720), transcript variant X2, mRNA", XP002801758, Database accession No. XM_008441955.
Database EMBL [Online] Dec. 31, 2009 (Dec. 31, 2009), "CsB10STC_Bam_61K17R_333 ends of BAC library of B10 line of Cucumis sativus L. (BamHI) Cucumis sativus genomic, genomic, survey sequence.", XP055767192, retrieved from EBI accession No. EMBL: GS860702 Database accession No. GS860702.
International Search Report issued in corresponding International Patent Application No. PCT/JP2018/028710 dated Oct. 23, 2018.
Kristkova et al., "Species spectra, distribution and host range of cucurbit powdery mildews in the Czech Republic, and in some other European and Middle Eastern countries," Phytoparasitica, 37: 337-350 (2009).

(Continued)

*Primary Examiner* — Weihua Fan
(74) *Attorney, Agent, or Firm* — Morgan, Lewis & Bockius LLP

(57) ABSTRACT

The present invention provides to a novel powdery mildew resistance marker for winter squash plants, a powdery mildew resistant winter squash plant, and a method for producing a powdery mildew resistant winter squash plant using the same. The powdery mildew resistance marker for winter squash plants according to the present invention is characterized in that it includes a powdery mildew resistance locus on chromosome 3.

20 Claims, 1 Drawing Sheet
Specification includes a Sequence Listing.

(56) References Cited

OTHER PUBLICATIONS

Zhang et al., "A high-density genetic map for anchoring genome sequences and identifying QTLs associated with dwarf vine in pumpkin (*Cucurbita maxima* Duch.)," BMC Genomics, 16 (1101): 1-13 (2015).

Holdsworth et al., "Cultivar-Based Introgression Mapping Reveals Wild Species-Derived Pm-0, the Major Powdery Mildew Resistance Locus in Squash," PLoS One, 11 (12): e0167715 (2016).

Vakalounakis et al., "Species spectrum, host range and distribution of powdery mildews on Cucurbitaceae in Crete," Plant Pathology, 43: 813-818 (1994).

Yamato, "Varieties ecology and characteristics," Squash, Basic edition, Growth stages, physiology, and ecology, Vegetables, Nogyogijutsutaikei, Rural Culture Association Japan, 5:126-2-126-7 (2007) (see partial English translation).

Morishita et al., "An Improved Evaluation Method for Screening and Selecting Powdery Mildew Resistant Cultivars and Lines of Cucumber (*Cucumis sativus* L.)," Journal of the Japanese Society for Horticultural Science, 71 (1): 94-100 (2002) (see English abstract).

Irving et al., "Changes in Carbohydrates and Carbohydrate Metabolizing Enzymes during the Development, Maturation, and Ripening of Buttercup Squash (*Cucurbita maxima* D. 'Delica')," Journal of the American Society for Horticultural Science, 122 (3): 310-314 (1997).

Office Action issued in corresponding Japanese Patent Application No. 2017-147647 dated Nov. 14, 2017.

Holdsworth WL et al. (2016) Cultivar-Based Introgression Mapping Reveals Wild Species-Derived Pm-0, the Major Powdery Mildew Resistance Locus in Squash. PLOS One 11(12): e0167715.

Contin, Maximo E., Jan. 1978, A Thesis Presented to the Faculty of the Graduate School of Cornell University, Interspecific Transfer of Powdery Mildew Resistance in the Genus *Cucurbita*.

\* cited by examiner

POWDERY MILDEW RESISTANCE MARKER FOR WINTER SQUASH PLANTS, POWDERY MILDEW RESISTANT WINTER SQUASH PLANT, METHOD FOR PRODUCING POWDERY MILDEW RESISTANT WINTER SQUASH PLANT USING THE SAME, AND METHOD FOR IMPARTING POWDERY MILDEW RESISTANCE TO WINTER SQUASH PLANT

SEQUENCE LISTING SUBMISSION VIA EFS-WEB

A computer readable text file, entitled "SequenceListing.txt," created on or about Jan. 28, 2020 with a file size of about 2 kb contains the sequence listing for this application and is hereby incorporated by reference in its entirety.

TECHNICAL FIELD

The present invention relates to a powdery mildew resistance marker for winter squash plants, a powdery mildew resistant winter squash plant, a method for producing a powdery mildew resistant winter squash plant using the same, and a method for imparting powdery mildew resistance to a winter squash plant.

BACKGROUND ART

In cultivation of squash plants, diseases caused by powdery mildew fungus occur frequently all over the world and are taken as serious problems worldwide. Plant bodies infected with the pathogen of the powdery mildew display white powdery spots on leaves and stems. Thereafter, withering of the leaves etc. occurs, which causes poor growth of the plants. As a result, the yield of fruits is reduced. Also, it is known that there are multiple types of powdery mildew fungi that cause powdery mildew in plants belonging to the genus *Cucurbita* (Non-Patent Literature 1).

In winter squash plants among the plants belonging to the genus *Cucurbita*, cultivars that are sufficiently resistant to the powdery mildew have not yet been produced. Therefore, there are demands for breeding of powdery mildew resistant cultivars of the winter squash plants.

CITATION LIST

Non-Patent Literature

[Non-Patent Literature 1] Eva Kristkova et. al., "Species spectra, distribution and host range of cucurbit powdery mildews in the Czech Republic, and in some other European and Middle Eastern countries", 2009, Phytoparasitica, vol. 37, pages 337-350

SUMMARY OF INVENTION

Technical Problem

With the foregoing in mind, it is an object of the present invention to provide a novel powdery mildew resistance marker for winter squash plants, a powdery mildew resistant winter squash plant, a method for producing a powdery mildew resistant winter squash plant using the same, and a method for imparting powdery mildew resistance to a winter squash plant.

Solution to Problem

In order to achieve the above object, the present invention provides a powdery mildew resistance marker for a winter squash plant (also referred to simply as "resistance marker" hereinafter) including: a powdery mildew resistance locus (also referred to simply as "resistance locus" hereinafter) on chromosome 3.

The present invention also provides a powdery mildew resistant winter squash plant (also referred to simply as "resistant winter squash plant" hereinafter) including a powdery mildew resistance locus on chromosome 3.

The present invention also provides a method for producing a powdery mildew resistant winter squash plant (also referred to simply as "production method" hereinafter), including the following steps (a) and (b):
(a) crossing the powdery mildew resistant winter squash plant according to the present invention with another winter squash plant; and
(b) selecting a powdery mildew resistant winter squash plant from one or more winter squash plants obtained in the step (a) or one or more progeny lines thereof.

The present invention also provides a method for imparting powdery mildew resistance to a winter squash plant (also referred to simply as "imparting method" hereinafter), including the step of: introducing a powdery mildew resistance locus on chromosome 3 to a winter squash plant.

Advantageous Effects of Invention

The inventors of the present invention conducted diligent studies, and discovered a novel powdery mildew resistance locus for winter squash plants as a powdery mildew resistance marker exhibiting powdery mildew resistance. A winter squash plant including the powdery mildew resistance marker exhibits powdery mildew resistance. Thus, the powdery mildew resistance marker for winter squash plants according to the present invention enables easy screening for powdery mildew resistant winter squash plants, for example. Also, the powdery mildew resistant winter squash plant according to the present invention includes the powdery mildew resistance locus, for example, and thus can exhibit powdery mildew resistance, for example. Accordingly, the powdery mildew resistant winter squash plant of the present invention can eliminate the necessity of prevention and extermination of powdery mildew using agricultural chemicals as performed conventionally, whereby problems of labor and cost for spraying the agricultural chemicals can be avoided, for example.

DESCRIPTION OF EMBODIMENTS

Figure 1:
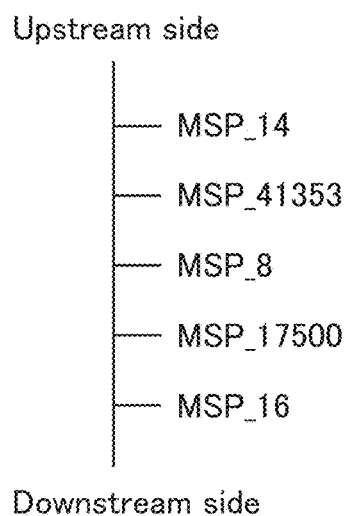
FIG. 1 is a schematic view showing relative locations of single nucleotide polymorphisms (SNPs) and the like on chromosome 3.

1. Powdery Mildew Resistance Marker for Winter Squash Plants

As described above, the powdery mildew resistance marker for a winter squash plant according to the present invention includes a powdery mildew resistance locus on chromosome 3. The powdery mildew resistance marker according to the present invention is characterized in that it includes the powdery mildew resistance locus on chromosome 3, and other configurations or conditions are not particularly limited.

In the present invention, a "winter squash plant" refers to a plant classified in *Cucurbita maxima* of the genus *Cucurbita*. The winter squash plant may be a hybrid with a related species, for example. Examples of the related species include *Cucurbita pepo* and *Cucurbita moschata*.

In the present invention, examples of the pathogen of powdery mildew (also referred to as "powdery mildew pathogen" hereinafter) include *Podosphaera xanthii* (also referred to as "*Sphaerotheca fuliginea*") and *Golovinomyces cichoracearum* (also referred to as "*Erysiphe cichoracearum*"). Among them, *Podosphaera xanthii* is preferable.

In the present invention, "powdery mildew resistance" also may be referred to as "powdery mildew tolerance", for example. The resistance means the ability to inhibit or suppress the occurrence and progression of damage due to the infection with the pathogen of powdery mildew, for example. Specifically, the resistance may mean any of the following, for example: to prevent the damage from occurring; to stop the progression of the damage that has occurred already; and to suppress (also referred to as "inhibit") the progression of the damage that has occurred already.

The winter squash plant has chromosomes 1 to 20. Each chromosome in the winter squash plant can be determined by comparing, for example, on the basis of the genome sequence information of *Cucurbita maxima* (cultivar name: Rimu), the genome sequence information of the winter squash plant to be examined with the genome sequence information of Rimu. The comparison can be performed by, for example, using analysis software such as BLAST or FASTA with default parameters. The genome sequence information of Rimu is available on the website (http://www.icugi.org/ or http://cucurbitgenomics.org/) of Cucurbit Genomics Database, for example.

Although the resistance marker according to the present invention includes the resistance locus on chromosome 3, a winter squash plant having the resistance locus may have the resistance locus on, instead of chromosome 3, any chromosome other than chromosome 3, for example. That is, the winter squash plant including the resistance locus may have the above-described resistance locus on chromosome 3 on any of chromosome 1, chromosome 2, chromosome 4, chromosome 5, chromosome 6, chromosome 7, chromosome 8, chromosome 9, chromosome 10, chromosome 11, chromosome 12, chromosome 13, chromosome 14, chromosome 15, chromosome 16, chromosome 17, chromosome 18, chromosome 19, and chromosome 20.

The resistance marker of the present invention may include resistance loci on chromosome 3 either in a heterozygous form or in a homozygous form, for example. In the latter case, the resistant winter squash plant may include at least one of the resistance markers on a chromosome other than chromosome 3. For example, the resistant winter squash plant may include one resistance locus on a chromosome other than chromosome 3 or two resistance loci on a chromosome(s) other than chromosome 3, for example. When the resistant winter squash plant includes two resistance loci on a chromosome(s) other than chromosome 3, the resistant winter squash plant may include the two resistance loci on the same chromosome or on different chromosomes, for example.

The powdery mildew resistance locus means a quantitative trait locus or a gene region that imparts the powdery mildew resistance. In general, the term "quantitative trait loci (QTL)" refers to chromosome regions involved in the expression of quantitative traits. The QTL can be specified using a molecular marker that indicates a specific locus on a chromosome. The technique for specifying the QTL using the molecular marker is well known in the art.

In the present invention, a molecular marker used for specifying the resistance locus is not particularly limited. Examples of the molecular marker include SNP markers, amplified fragment length polymorphism (AFLP) markers, restriction fragment length polymorphism (RFLP) markers, microsatellite markers, sequence-characterized amplified region (SCAR) markers, and cleaved amplified polymorphic sequence (CAPS) markers. In the present invention, one SNP marker may be used, or two or more SNP markers may be used in combination, for example.

In the present invention, the powdery mildew resistance locus may be specified (also referred to as "identified" hereinafter) by, for example: (1) the SNP marker; (2) a base sequence including the SNP marker; (3) a base sequence in a region between sites of two SNP markers; or any combination thereof. When the powdery mildew resistance locus is specified by any combination of (1) to (3), the combination is not particularly limited, and examples thereof include the following combinations:

the combination of (1) and (2);
the combination of (1) and (3);
the combination of (2) and (3); and
the combination of (1), (2), and (3).

(1) Identification by SNP Marker

The resistance locus may be specified by the SNP marker, as described in the item (1) above, for example. The SNP marker is not particularly limited, and examples thereof include MSP_17500, MSP_8, and MSP_41353. As to the analysis of these SNPs, the reference literature 1 shown below can be referred to, for example. MSP_17500, MSP_8, and MSP_41353 are SNP markers newly identified by the inventors of the present invention, and those skilled in the art can identify the chromosomal locations of these SNP markers on the basis of the base sequences including the SNP markers to be described below.

Reference literature 1: Guoyu Zhang et. al. (2015) "A high-density genetic map for anchoring genome sequences and identifying QTLs associated with dwarf vine in pumpkin (*Cucurbita maxima* Duch.)", BMC Genomics, 16:1101

MSP_17500 (also referred to as "SNP (a)" hereinafter) is a polymorphism such that the underlined base in brackets in SEQ ID NO: 1 shown below (the 37th base in SEQ ID NO: 1) is C. That is, for example, a winter squash plant is resistant to powdery mildew when the SNP (a) is C, and is susceptible to powdery mildew when the SNP (a) is a base other than C (e.g., T). The base sequence of SEQ ID NO: 1 can be obtained from the winter squash plant deposited under Accession No. FERM BP-22336 to be described below, for example. The SNP (a) can be identified on the basis of known information in the database of the above-described web site etc., for example.

SEQ ID NO: 1
5'-CTTCATATTGTTTTGTGGTACACCATAAGCCAAGTA[C]GCCTT

TCAGAAAACAAAGTAGATATTATAGCCTGACTGTCTATGAAGAACTA

AAAAG-3'

MSP_8 (also referred to as "SNP (b)" hereinafter) is a polymorphism such that the underlined base in brackets in SEQ ID NO: 2 shown below (the 59th base in SEQ ID NO: 2) is T. That is, for example, a winter squash plant is resistant to powdery mildew when the SNP (b) is T, and is susceptible to powdery mildew when the SNP (b) is a base other than T (e.g., G). The base sequence of SEQ ID NO: 2 can be obtained from the winter squash plant deposited under Accession No. FERM BP-22336 to be described below, for example. The SNP (b) can be identified on the basis of known information in the database of the above-described web site etc., for example.

SEQ ID NO: 2
5'-ACATCTGAAAAAGTTGAAGCTGTTATGTGATGGAGAGATTGCAG

AGTGGTTGAAAACG[T]TTGCTCCCCACCTTGCCAAACAGGT

CAAA-3'

MSP_41353 (also referred to as "SNP (c)" hereinafter) is a polymorphism such that the underlined base in brackets in SEQ ID NO: 3 shown below (the 34th base in SEQ ID NO: 3) is C. That is, for example, a winter squash plant is resistant to powdery mildew when the SNP (c) is C, and is susceptible to powdery mildew when the SNP (a) is a base other than C (e.g., T). The base sequence of SEQ ID NO: 3 can be obtained from the winter squash plant deposited under Accession No. FERM BP-22336 to be described below, for example. The SNP (c) can be identified on the basis of known information in the database of the above-described web site etc., for example.

SEQ ID NO: 3
5'-GAGAGTGGGCAACAATTTCCCCTTGAAGAAGAG[C]TCGTCGGC

GGCGGTCATTGTGTGATTACTGGGA-3'

The locations of the SNP markers on the chromosome are not particularly limited. For example, as shown in FIG. 1, on chromosome 3 of a winter squash plan, MSP_41353, MSP_8, and MSP_17500 are located in this order from the upstream side (MSP_14 side) toward the downstream side (MSP_16 side). In FIG. 1, MSP_16 and MSP_14 are used merely to indicate the chromosomal locations of MSP_17500, MSP_8, and MSP_41353 on chromosome 3 of the winter squash plant. It is to be noted that either one or both of MSP_16 and MSP_14 may be used as an SNP marker(s). In this case, in descriptions regarding MSP_16 and MSP_14 to be provided below, a winter squash plant is resistant to powdery mildew when MSP_16 or MSP_14 is a polymorphism of the winter squash plant deposited under Accession No. FERM BP-22336 and is susceptible to powdery mildew when MSP_16 or MSP_14 is a base other than the polymorphism of the winter squash plant deposited under Accession No. FERM BP-22336. When at least one of MSP_16 and MSP_14 is used as a SNP marker, at least one of MSP_16 and MSP_14 may be used in combination with at least one SNP marker selected from the group consisting of MSP_17500, MSP_8, and MSP_41353.

The number of the SNP markers present in the resistance locus is not particularly limited. For example, the resistance locus may include any one of the SNP markers or two or more of the SNP markers (i.e., two SNP markers or all the three SNP markers). The relevance of these three types of polymorphisms (SNP markers) with the powdery mildew resistance has not been reported heretofore. They are novel polymorphisms discovered first by the inventors of the present invention as being involved in the powdery mildew resistance.

The combination of the SNP markers is not particularly limited, and examples thereof include the following combinations:
the combination of SNP (a) and SNP (b);
the combination of SNP (a) and SNP (c);
the combination of SNP (b) and SNP (c); and
the combination of SNP (a), SNP (b), and SNP (c).
Among these combinations, for example, the following combination is preferable because the resistance locus shows higher correlation with the powdery mildew resistance:
the combination of SNP (a), SNP (b), and SNP (c).

(2) Identification by Base Sequence Including SNP Marker

The resistance locus may be specified by a base sequence including the SNP marker, as described in the above item (2), for example. The resistance locus may consist of the base sequence or may include the base sequence, for example.

The base sequence including the SNP marker is not particularly limited, and examples thereof include the following polynucleotides (a), (b), and (c). The polynucleotides (a), (b), and (c) correspond to base sequences including the SNP markers, namely, the SNPs (a), (b), and (c), respectively.

The polynucleotide (a) is a base sequence including the SNP (a), i.e., MSP_17500. Examples of the polynucleotide (a) include the following polynucleotides (a1), (a2), and (a3). The polynucleotides (a2) and (a3) are polynucleotides each having, in the resistance locus, a function equivalent to that of the polynucleotide (a1) regarding the powdery mildew resistance. The equivalent function means that, for example, a winter squash plant having a powdery mildew resistance locus identified by the polynucleotide (a2) or (a3) is resistant to powdery mildew.

(a) the following polynucleotide (a1), (a2), or (a3)
(a1) a polynucleotide consisting of the base sequence of SEQ ID NO: 1
(a2) a polynucleotide consisting of a base sequence obtained by deletion, substitution, insertion, and/or addition of one or more bases in the base sequence of the polynucleotide (a1) with the 37th base (C) in the base sequence of the polynucleotide (a1) being conserved
(a3) a polynucleotide consisting of a base sequence having at least 80% sequence identity to the base sequence of the polynucleotide (a1) with the 37th base (C) in the base sequence of the polynucleotide (a1) being conserved In the polynucleotide (a1), the underlined base (C) in the brackets in SEQ ID NO: 1 is a base corresponding to the polymorphism of the SNP (a). The polynucleotide (a1) can be obtained from the winter squash plant deposited under Accession No. FERM BP-22336 to be described below, for example.

In the polynucleotide (a2), the number of the "one or more" bases is, for example, 1 to 18, 1 to 12, 1 to 8, 1 to 4, 1 to 3, 1, or 2. In the present invention, the numerical range regarding the number of bases discloses all the positive integers falling within that range, for example. That is, for example, the description "one to five bases" discloses all of "one, two, three, four, and five bases" (the same applies hereinafter).

In the polynucleotide (a3), the "sequence identity" is, for example, at least 80%, at least 85%, at least 89%, at least 90%, at least 95%, at least 96%, at least 97%, at least 98%, or at least 99%. The "sequence identity" can be determined by aligning two base sequences (the same applies hereinafter). Specifically, the sequence identity can be calculated by, for example, using analysis software such as BLAST or FASTA with default parameters (the same applies hereinafter).

The polynucleotide (b) is a base sequence including the SNP (b), i.e., MSP_8. Examples of the polynucleotide (b) include the following polynucleotides (b1), (b2), and (b3). The polynucleotides (b2) and (b3) are polynucleotides each having, in the resistance locus, a function equivalent to that of the polynucleotide (b1) regarding the powdery mildew resistance. The equivalent function means that, for example, a winter squash plant having a powdery mildew resistance locus identified by the polynucleotide (b2) or (b3) is resistant to powdery mildew.

(b) the following polynucleotide (b1), (b2), or (b3)
(b1) a polynucleotide consisting of the base sequence of SEQ ID NO: 2
(b2) a polynucleotide consisting of a base sequence obtained by deletion, substitution, insertion, and/or addition of one or more bases in the base sequence of the polynucleotide (b1) with the 59th base (T) in the base sequence of the polynucleotide (b1) being conserved
(b3) a polynucleotide consisting of a base sequence having at least 80% sequence identity to the base sequence of the polynucleotide (b1) with the 59th base (T) in the base sequence of the polynucleotide (b1) being conserved In the polynucleotide (b1), the underlined base (T) in the brackets in SEQ ID NO: 2 is a base corresponding to the polymorphism of the SNP (b). The polynucleotide (b1) can be obtained from the winter squash plant deposited under Accession No. FERM BP-22336 to be described below, for example.

In the polynucleotide (b2), the number of the "one or more" bases is, for example, 1 to 17, 1 to 13, 1 to 8, 1 to 4, 1 to 3, 1, or 2.

In the polynucleotide (b3), the "sequence identity" is, for example, at least 80%, at least 85%, at least 89%, at least 90%, at least 95%, at least 96%, at least 97%, at least 98%, or at least 99%.

In the polynucleotides (b2) and (b3), it is preferable that at least one of the 60th base (T) and the 62nd base (G) underlined in the base sequence of the polynucleotide (b1) is conserved. In this case, to the "one or more" bases and the "sequence identity", the descriptions regarding the "one or more" bases and the "sequence identity" provided above in connection with the polynucleotides (b2) and (b3) also apply, respectively.

The polynucleotide (c) is a base sequence including the SNP (c), i.e., MSP_41353. Examples of the polynucleotide (c) include the following polynucleotides (c1), (c2), and (c3). The polynucleotides (c2) and (c3) are polynucleotides each having, in the resistance locus, a function equivalent to that of the polynucleotide (c1) regarding the powdery mildew resistance. The equivalent function means that, for example, a winter squash plant having a powdery mildew resistance locus identified by the polynucleotide (c2) or (c3) is resistant to powdery mildew.

(c) the following polynucleotide (c1), (c2), or (c3)
(c1) a polynucleotide consisting of the base sequence of SEQ ID NO: 3
(c2) a polynucleotide consisting of a base sequence obtained by deletion, substitution, insertion, and/or addition of one or more bases in the base sequence of the polynucleotide (c1) with the 34th base (C) in the base sequence of the polynucleotide (c1) being conserved
(c3) a polynucleotide consisting of a base sequence having at least 80% sequence identity to the base sequence of the polynucleotide (c1) with the 34th base (C) in the base sequence of the polynucleotide (c1) being conserved In the polynucleotide (c1), the underlined base (C) in the brackets in SEQ ID NO: 3 is a base corresponding to the polymorphism of the SNP (c). The polynucleotide (c1) can be obtained from the winter squash plant deposited under Accession No. FERM BP-22336 to be described below, for example.

In the polynucleotide (c2), the number of the "one or more" bases is, for example, 1 to 13, 1 to 6, 1 to 3, 1, or 2.

In the polynucleotide (c3), the "sequence identity" is, for example, at least 80%, at least 85%, at least 89%, at least 90%, at least 95%, at least 96%, at least 97%, at least 98%, or at least 99%.

The number of the base sequences including the SNP markers in the resistance locus is not particularly limited. For example, the resistance locus may include any one of the polynucleotides (a), (b), and (c) or two or more of the polynucleotides (a), (b), and (c) (i.e., two selected from the polynucleotides (a), (b), and (c) or all the three polynucleotides (a), (b), and (c)).

The combination of the base sequences including the SNP markers is not particularly limited, and examples thereof include the following combinations:
the combination of the polynucleotides (a) and (b);
the combination of the polynucleotides (a) and (c);
the combination of the polynucleotides (b) and (c);
the combination of the polynucleotides (a), (b), and (c);
Among these combinations, for example, the following combination is preferable because the resistance locus shows higher correlation with the powdery mildew resistance:
the combination of the polynucleotides (a), (b), and (c).

As the base sequence(s) including the SNP marker(s), at least one of a base sequence including MSP_16 (a polynucleotide consisting of a base sequence of SEQ ID NO: 4) to be described below and a base sequence including MSP_14 (a polynucleotide consisting of a base sequence of SEQ ID NO: 5) to be described below may be used, for example. In this case, each polynucleotide may be, for example, a polynucleotide consisting of a base sequence obtained by deletion, substitution, insertion, and/or addition of one or more bases in the base sequence of each polynucleotide with a base corresponding to the polymorphism or an underlined base(s) in the base sequence of each polynucleotide being conserved, or a polynucleotide consisting of a base sequence having at least 80% sequence identity to the base sequence of each polynucleotide with the base corresponding to the polymorphism or the underlined base(s) in the base sequence of each polynucleotide being conserved. The descriptions regarding the "one or more" bases and the "sequence identity" provided above in connection with the polynucleotides (a2) and (a3) also apply to the "one or more" bases and the "sequence identity" in the above, respectively. Each polynucleotide may be used in combination with at least one polynucleotide selected from the group consisting of the polynucleotides (a), (b), and (c), for example.

(3) Identification by Base Sequence in Region Between Sites of Two SNP Markers

The resistance locus may be specified by the base sequence in a region between sites of two SNP markers, as described in the item (3), for example. The base sequence in a region between sites of the two SNP markers is not particularly limited, and may be, for example, a base sequence in a region between sites of two SNP markers selected from the group consisting of MSP_16, MSP_17500, MSP_8, MSP_41353, and MSP_14 on the chromosome. Regarding the base sequence in a region between sites of the two SNP markers, reference can be made to the base sequence in a region between sites of corresponding two SNP markers in the winter squash plant deposited under Accession No. FERM BP-22336 to be described below (also referred to as "deposited line" hereinafter), for example. When reference is made to the base sequence of the deposited line, the base sequence in a region between sites of the two SNP markers agree with the base sequence in the deposited line completely or partially, for example. In the latter case, the base sequence in the region between the sites of the two SNP markers may be such that, for example, a winter squash plant having a resistance locus identified by the base sequence in the region between the sites of the two SNP markers is resistant to powdery mildew. The above-described partial agreement can be specified by, for example, the sequence identity to the base sequence in the deposited line. The sequence identity is, for example, at least 80%, at least 85%, at least 89%, at least 90%, at least 95%, at least 96%, at least 97%, at least 98%, or at least 99%. When the resistance locus is identified by the base sequence described in the above item (3), it also can be said that the resistance locus is located on the region between the sites of the two SNP markers, for example.

The MSP_16 (also referred to as "SNP (d)" hereinafter) is a polymorphism at the underlined base in brackets in SEQ ID NO: 4, for example. In the winter squash plant deposited under Accession No. FERM BP-22336 to be described below, the SNP (d) is a polymorphism such that the underlined base in the brackets is G. However, the SNP (d) may be a base other than G, i.e., A, T, or C, for example. The base sequence of SEQ ID NO: 4 can be obtained from the winter squash plant deposited under Accession No. FERM BP-22336 to be described below, for example. The SNP (d) can be identified on the basis of known information in the database of the above-described web site etc., for example.

SEQ ID NO: 4
5'-ATGAGGAATGATTACGTTTGGAAACTTTGCAGGTTGTGGGAGT

[G]CTGGTTGGCAAGCCCCTGAACAACTTCTT-3'

The MSP_14 (also referred to as "SNP (e)" hereinafter) is a polymorphism at the underlined base in brackets in SEQ ID NO: 5, for example. In the winter squash plant deposited under Accession No. FERM BP-22336 to be described below, the SNP (e) is a polymorphism such that the underlined base in the brackets is C. However, the SNP (e) may be a base other than C, i.e., A, T, or G, for example. The base sequence of SEQ ID NO: 5 can be obtained from the winter squash plant deposited under Accession No. FERM BP-22336 to be described below, for example. The SNP (e) can be identified on the basis of known information in the database of the above-described web site etc., for example.

SEQ ID NO: 5
5'-ATTGT<u>C</u>AC<u>T</u>AGAATTTGGCCAAACACTAAGTACCTGGATGTGA

TTGTGAC[<u>C</u>]GGAGCCATGGCTCAGTACATACCCACCTTGGAACTT

TACAGTGGAGGG<u>T</u>TACCCATGGCTTGCAC<u>T</u>ATG-3'

The upstream-side end and the downstream-side end of the region can be identified by, for example, the sites of the two SNP markers, as described above. The region is not limited as long as it extends between the sites of the two SNP markers, for example. The region may or may not include both or one of the sites of the two SNP markers, for example. When the region includes the sites of the SNP markers, the upstream-side end and the downstream-side end of the region are the sites of the SNP markers. The bases at the upstream-side end and the downstream-side end may each be the above-described underlined base in the base sequence or may be a base other than the underlined base, for example.

The two SNP markers specifying the region are not particularly limited, and examples thereof include the following combinations:
the combination of SNP (a) and SNP (c);
the combination of SNP (a) and SNP (e);
the combination of SNP (c) and SNP (d); and
the combination of SNP (d) and SNP (e).

In the case where the resistance locus is specified by the base sequence in a region between sites of the two SNP markers, it is preferable that the resistance locus further includes, in the base sequence in the region, the SNP marker(s) located in the region. Specifically, it is preferable that the resistance locus includes, in the base sequence in the region, at least one SNP marker selected from the group consisting of MSP_17500, MSP_8, and MSP_41353, for example.

The SNP marker(s) located in the region may be, for example, one or both of the sites of the two SNP markers specifying the region on the chromosome, or may be the SNP marker(s) located between the sites of the two SNP markers specifying the region. The former also is referred to as a SNP marker(s) at the end(s) of the region, and the latter also is referred to as a SNP marker(s) inside the region. The SNP markers located in the region may be both the SNP markers at the ends of the region and the SNP marker(s) inside the region, for example.

The SNP marker(s) inside the region may be, for example, a SNP marker(s) located between the SNP marker on the upstream side and the SNP marker on the downstream side specifying the region, and can be determined as appropriate on the basis of the locations of the SNP markers shown in FIG. 1, for example. The number of the SNP markers between the sites of the two SNP markers may be one or more, for example. As a specific example, the SNP markers may be all the SNP markers located between the sites of the SNP markers specifying the region.

The combination of the base sequence in a region between sites of the two SNP markers and the SNP marker(s) in the base sequence in the region is not particularly limited, and may satisfy the following condition (i) or (ii), for example.
Condition (i)
The resistance locus includes a base sequence in a region between sites of SNP (a) and SNP (c) on the chromosome, and
the resistance locus also includes, in the base sequence in the region, SNP (b) or at least one SNP marker selected from the group consisting of SNP (a), SNP (b), and SNP (c).
Condition (ii)
The resistance locus includes a base sequence in a region between sites of SNP (d) and SNP (e) on the chromosome, and
the resistance locus also includes, in the base sequence in the region, SNP (b) or at least one SNP marker selected from the group consisting of SNP (a), SNP (b), and SNP (c).

The resistance locus is, for example, a powdery mildew resistance locus on chromosome 3 of the powdery mildew resistant winter squash plant deposited under Accession No. FERM BP-22336 to be described below.

The powdery mildew resistance marker according to the present invention can impart powdery mildew resistance to winter squash plants, for example. In the present invention, the degree of the powdery mildew resistance of a winter squash plant can be expressed by the severity of powdery mildew, which is calculated on the basis of the disease index evaluated in accordance with a method in Example 1 to be described below. Regarding the calculation of the severity according to this method, reference can be made to explanation in Example 1 to be described below, and the disease index of less than 2 can be evaluated as being tolerant to powdery mildew and the disease index of 2 or more can be evaluated as being susceptible to powdery mildew, for example. When the powdery mildew resistance is determined according to the severity, the severity may be, for example, the severity of a single winter squash plant or the average severity of two or more winter squash plants, and the latter is preferable. In the latter case, the number of winter squash plants used for determining the powdery mildew resistance is not particularly limited, and may be, for example, sufficient to conduct statistical test in comparison with powdery mildew susceptible winter squash plants. As a specific example, the number of winter squash plants may be 5 to 20, or 5.

2. Powdery Mildew Resistant Winter Squash Plant

As described above, the powdery mildew resistant winter squash plant according to the present invention includes a powdery mildew resistance locus on chromosome 3. The powdery mildew resistant winter squash plant according to the present invention is characterized in that it includes the powdery mildew resistance locus on chromosome 3, and other configurations or conditions are not particularly limited. The powdery mildew resistant winter squash plant according to the present invention includes the powdery mildew resistance marker of the present invention, which includes the powdery mildew resistance locus. Thus, the above description regarding the powdery mildew resistance marker for winter squash plants according to the present invention also applies to the powdery mildew resistant winter squash plant according to the present invention, for example. In the present invention, the powdery mildew resistance locus on chromosome 3 should be interpreted as interchangeable with the powdery mildew resistance marker according to the present invention, for example.

The powdery mildew resistant winter squash plant of the present invention is resistant to powdery mildew.

In the powdery mildew resistant winter squash plant of the present invention, the powdery mildew resistance is imparted by the powdery mildew resistance locus on chromosome 3, as described above. Although the powdery mildew resistant winter squash plant of the present invention has the resistance locus on chromosome 3, it may have the powdery mildew resistance locus on chromosome 3 on, instead of chromosome 3, any chromosome other than chromosome 3, for example. That is, the winter squash plant including the resistance locus may have the above-described resistance locus on chromosome 3 on any of chromosome 1, chromosome 2, chromosome 4, chromosome 5, chromosome 6, chromosome 7, chromosome 8, chromosome 9, chromosome 10, chromosome 11, chromosome 12, chromosome 13, chromosome 14, chromosome 15, chromosome 16, chromosome 17, chromosome 18, chromosome 19, and chromosome 20.

The resistant winter squash plant of the present invention may include, for example, one resistance locus or two or more resistance loci. As a specific example, one of a pair of homologous chromosomes may include the resistance locus (heterozygous form) or both the homologous chromosomes may include the resistance loci (homozygous form). The latter is preferable because the resistant winter squash plant exhibits higher powdery mildew resistance.

To the above-described resistance locus in the winter squash plant of the present invention, the description regarding the powdery mildew resistance locus provided above in connection with the powdery mildew resistance marker for winter squash plants according to the present invention also applies, for example.

The powdery mildew resistant winter squash plant of the present invention may be, for example, the winter squash plant deposited under Accession No. FERM BP-22336 (*Cucurbita maxima*) or a progeny line thereof. The progeny line has the resistance locus, for example. The information on the deposit is shown below.

Type of deposit: International deposit
Name of depository institution: National Institute of Technology and Evaluation, International Patent Organism Depositary; NITE-IPOD
Address: 2-5-8-120, Kazusakamatari, Kisarazu-shi, Chiba 292-0818, Japan
Accession No. FERM BP-22336
Identifying designation: Takii10
Date of acceptance: Jun. 1, 2017

The resistant winter squash plant according to the present invention can be produced by, for example, introducing the resistance locus to a winter squash plant. The method for introducing the resistance locus to a winter squash plant is not particularly limited, and the resistance locus may be introduced by crossing with the resistant winter squash plant, embryo culture, or a conventionally known genetic engineering procedure, for example. Examples of the resistance locus to be introduced include those given above as examples of the resistance locus. When the resistance locus is introduced by crossing with the resistant winter squash plant, the resistant winter squash plant preferably includes the resistance loci in a homozygous form, for example.

There is no particular limitation on the characteristics of the powdery mildew resistant winter squash plant of the present invention other than the powdery mildew resistance, such as, for example, morphological characteristics and biological characteristics.

The powdery mildew resistant winter squash plant of the present invention may also have any other resistance.

The term "plant body" as used in the present invention may refer to either a plant individual representing the whole plant or a part of the plant individual. The part of the plant individual may be any of organs, tissues, cells, and propagules, for example. Examples of the organs include petals, corollas, flowers, leaves, seeds, fruits, stems, and roots. The tissue is a part of the organ, for example. The part of the plant body may be one type of organ, tissue, and/or cell, or two or more types of organs, tissues, and/or cells, for example.

3. Method for Producing Powdery Mildew Resistant Winter Squash Plant

Next, the method for producing a powdery mildew resistant winter squash plant according to the present invention will be described. It is to be noted, however, that methods to be described below are merely illustrative, and the present invention is by no means limited to these methods. In the present invention, the production method also can be referred to as a "growing method", for example. Also, in the present invention, the powdery mildew resistance locus should be interpreted as interchangeable with the resistance marker according to the present invention, and the above description regarding the resistance marker of the present invention also applies to the powdery mildew resistance locus.

As described above, the method for producing a powdery mildew resistant winter squash plant according to the present invention includes the following steps (a) and (b):
(a) crossing the powdery mildew resistant winter squash plant according to the present invention with another winter squash plant; and
(b) selecting a powdery mildew resistant winter squash plant from one or more winter squash plants obtained in the step (a) or one or more progeny lines thereof.

The production method according to the present invention is characterized in that the powdery mildew resistant winter squash plant according to the present invention is used as a parent, and other steps or conditions are not limited by any means. The above descriptions regarding the resistance marker and powdery mildew resistant winter squash plant according to the present invention etc. also apply to the production method of the present invention, for example.

In the step (a), a powdery mildew resistant winter squash plant used as a first parent is not limited as long as it is the powdery mildew resistant winter squash plant of the present invention. Preferably, the powdery mildew resistant winter squash plant is the above-described winter squash plant deposited under Accession No. FERM BP-22336 or a progeny line thereof, for example. The powdery mildew resistant winter squash plant used as the first parent in the step (a) also can be obtained by a screening method of the present invention to be described below, for example. Thus, the powdery mildew resistant winter squash plant may be provided by, for example, selecting it from one or more winter squash plants to be examined (also referred to as "candidate winter squash plants") by performing the following step (x) prior to the step (a), for example:
(x) selecting the powdery mildew resistant winter squash plant of the present invention from one or more winter squash plants to be examined.

In the step (x), the selection of the powdery mildew resistant winter squash plant can be referred to as selection of the winter squash plant having the resistance locus. Thus, the step (x) can be carried out by the following steps (x1) and (x2), for example:
(x1) detecting the presence or absence of the powdery mildew resistance locus on a chromosome(s) of each of the one or more winter squash plants to be examined; and
(x2) selecting, as a powdery mildew resistant winter squash plant(s), one or more winter squash plants to be examined having the powdery mildew resistance locus.

As described above, the selection in the step (x) is the selection of the winter squash plant including the resistance locus, for example. Specifically, the powdery mildew resistant winter squash plant can be selected by carrying out detection of the powdery mildew resistance locus with respect to the one or more winter squash plants to be examined. In the step (x2), for example, the winter squash plant to be examined may be selected as the resistant winter squash plant when the resistance locus is present in one of a pair of homologous chromosomes, or the winter squash plant to be examined may be selected as the resistant winter squash plant when the resistance locus is present in each of the pair of homologous chromosomes, and the latter is preferable. The detection of the resistance locus in the step (x1) can be performed using, for example, as described above in connection with the powdery mildew resistance marker of the present invention, any of the following (1) to (3) specifying the powdery mildew resistance locus or any combination thereof: (1) the SNP marker; (2) a base sequence including the SNP marker; and (3) a base sequence in a region between sites of two SNP markers.

The selection in the step (x) will be described with reference to the following specific example. It is to be noted, however, that the present invention is not limited thereto. The description regarding the powdery mildew resistance locus provided above in connection with the resistance marker of the present invention also applies to the powdery mildew resistance locus in the production method of the present invention.

(1) Identification by SNP Marker

The selection in the step (x) is, for example, selection of a winter squash plant including a powdery mildew resistance locus identified by at least one SNP marker selected from the group consisting of MSP_17500, MSP_8, and MSP_41353. The SNP marker to be selected is not particularly limited, and the description in the "(1) Identification by SNP marker" provided above in connection with the powdery mildew resistance marker of the present invention also applies, for example.

(2) Identification by Base Sequence Including SNP Marker

The selection in the step (x) is, for example, selection of a winter squash plant including a powdery mildew resistance locus identified by at least one polynucleotide selected from the group consisting of the polynucleotides (a), (b), and (c). Regarding the polynucleotides (a), (b), and (c), the description in the "(2) Identification by base sequence including SNP marker" provided above in connection with the resistance marker of the present invention also applies, for example.

(3) Identification by Base Sequence in Region Between Sites of Two SNP Markers

The selection in the step (x) is, for example, selection of a winter squash plant including a powdery mildew resistance locus that includes a base sequence in a region between sites of two SNP markers selected from the group consisting of MSP_16, MSP_17500, MSP_8, MSP_41353, and MSP_14 on the chromosome. Regarding the base sequence in a region between sites of the two SNP markers, the description in the "(3) Identification by base sequence in region between sites of two SNP markers" provided above in connection with the powdery mildew resistance marker of the present invention also applies, for example.

As a specific example, the selection in the step (x) may be, for example, selection of a winter squash plant that has a powdery mildew resistance locus including, in the base sequence in the region, at least one SNP marker selected from the group consisting of MSP_17500, MSP_8, and MSP_41353.

Also, the selection in the step (x) may be selection of a winter squash plant including a powdery mildew resistance locus that satisfies the above-described condition (i) or (ii), for example.

The chromosome to be subjected to the detection of the presence or absence of the powdery mildew resistance locus preferably is chromosome 3.

In the step (a), the winter squash plant to be used as the other parent is not particularly limited, and may be, for example, a winter squash plant with or without a known powdery mildew resistance, a winter squash plant with or without any other resistance, or the powdery mildew resistant winter squash plant of the present invention.

In the step (a), the method for crossing the powdery mildew resistant winter squash plant with another winter squash plant is not particularly limited, and a known method can be employed.

In the step (b), winter squash plants from which a powdery mildew resistant winter squash plant is to be selected may be the winter squash plants obtained in the step (a) or progeny lines obtained from these winter squash powdery mildew resistant winter squash plants, for example. Specifically, for example, the winter squash plants from which a powdery mildew resistant winter squash plant is to be selected may be F1-hybrid winter squash plants obtained by the crossing in the step (a) or their progeny lines. The progeny line may be a selfed progeny or a backcross progeny of the F1-hybrid winter squash plants obtained by the crossing in the step (a), or may be a winter squash plant obtained by crossing the F1-hybrid winter squash plant with another winter squash plant, for example.

In the step (b), the selection of a powdery mildew resistant winter squash plant can be achieved by, for example, examining the powdery mildew resistance directly or indirectly.

In the step (b), the direct examination can be carried out by evaluating the powdery mildew resistance of the obtained F1-hybrid winter squash plant or a progeny line thereof on the basis of the above-described severity, for example. Specifically, for example, the direct examination can be carried out by inoculating the F1-hybrid winter squash plant or the progeny line thereof with powdery mildew fungus and evaluating the powdery mildew resistance on the basis of the severity. In this case, for example, the F1-hybrid winter squash plant or the progeny line showing the severity of lower than 2 can be selected as the powdery mildew resistant winter squash plant.

In the step (b), the selection by the indirect examination can be carried out by the following steps (b1) and (b2), for example:

(b1) detecting the presence or absence of a powdery mildew resistance locus on a chromosome(s) of each of the winter squash plants obtained in the step (a) or one or more progeny lines thereof; and (b2) selecting, as a powdery mildew resistant winter squash plant(s), one or more winter squash plants obtained in the step (a) or one or more progeny lines thereof having the powdery mildew resistance locus.

The selection of the powdery mildew resistant winter squash plant(s) in the step (b) by the indirect examination is, for example, the selection performed in the same manner as in the step (x), and can be performed by detecting the presence or absence of the powdery mildew resistance locus. More specifically, the selection can be performed by detecting the presence or absence of the powdery mildew resistance locus using the molecular marker.

The production method of the present invention preferably further includes growing the powdery mildew resistant winter squash plant selected in the step (b).

The winter squash plant or the progeny line demonstrated to be powdery mildew resistant in the above-described manner can be selected as the powdery mildew resistant winter squash plant.

The production method of the present invention may further include the step of collecting seeds from the progeny line obtained by the crossing.

The production method of the present invention may include only the step (a), for example.

4. Screening Method for Powdery Mildew Resistant Winter Squash Plants

The screening method for a powdery mildew resistant winter squash plant according to the present invention (also referred to simply as "screening method" hereinafter) includes the step of: as a parent for producing a powdery mildew resistant winter squash plant by crossing, selecting a winter squash plant including, as a powdery mildew resistance marker for a winter squash plant, a powdery mildew resistance locus on chromosome 3 from one or more winter squash plants to be examined.

The screening method of the present invention is characterized in that it includes the step of selecting a plant including, as a powdery mildew resistance marker for a winter squash plant, a powdery mildew resistance locus on chromosome 3 from one or more winter squash plants to be examined, and other steps or conditions are not limited by any means. According to the screening method of the present invention, a powdery mildew resistant parent can be obtained by using the powdery mildew resistance marker of the present invention. The above descriptions regarding the resistance marker, powdery mildew resistant winter squash plant, and production method according to the present invention etc. also apply to the screening method of the present invention, for example.

To the selection of the parent, the description regarding the step (x) provided above in connection with the method for producing a powdery mildew resistant winter squash plant according to the present invention also applies, for example.

5. Method for Imparting Powdery Mildew Resistance to Winter Squash Plants

The method for imparting powdery mildew resistance to a winter squash plant according to the present invention includes the step of: introducing a powdery mildew resistance locus on chromosome 3 to a winter squash plant. The imparting method according to the present invention is characterized in that it includes the step of introducing a powdery mildew resistance locus on chromosome 3 to a winter squash plant, and other steps or conditions are not particularly limited. According to the imparting method of the present invention, it is possible to impart powdery mildew resistance to a winter squash plant by introducing the powdery mildew resistance locus on chromosome 3, i.e., the powdery mildew resistance marker of the present invention. The above descriptions regarding the resistance marker, powdery mildew resistant winter squash plant, production method, and screening method according to the present invention etc. also apply to the imparting method of the present invention, for example.

In the above-described introducing step, the method for introducing the powdery mildew resistance locus on chromosome 3 is not particularly limited. The method for introducing the resistance locus may be, for example, crossing with the resistant winter squash plant, embryo culture, or a conventionally known genetic engineering procedure. Examples of the resistance locus to be introduced include those given above as examples of the resistance locus. When the resistance locus is introduced by crossing with the resistant winter squash plant, the resistant winter squash plant preferably includes the resistance loci in a homozygous form, for example.

EXAMPLES

The present invention will be described specifically below with reference to examples. It is to be noted, however, that the present invention is by no means limited to embodiments described in the following examples.

Example 1

The present example examined whether novel powdery mildew resistant winter squash plants are resistant to powdery mildew fungus. The present example also analyzed the mode of inheritance of powdery mildew resistance loci and identified novel powdery mildew resistance loci.

In order to develop novel winter squash plants resistant to powdery mildew, a large amount of seeds collected from winter squash lines obtained by subculture breeding in a farm owned by TAKII & CO., LTD. were grown and the powdery mildew resistance of the thus-obtained winter squash lines was examined. As a result, a novel powdery mildew resistance winter squash line (Cucurbita maxima) exhibiting powdery mildew resistance was obtained. Hereinafter, the line of these powdery mildew resistant winter squash plants is referred to as a "parental line".

Also, separately from the parental line, an F2 population was produced by crossing a powdery mildew resistant line and a powdery mildew susceptible line, and DNAs were extracted from the F2 population. Then, the thus-extracted DNAs were subjected to Sequence-Based Genotyping (Keygene). Further, linkage maps were prepared using software (Carte Blanche, Keygene) and linkage analysis was conducted using software (QTL cartographer, NC STATE University. As a result, one QTL exhibiting a peak LOD value of 25.8 (the LOD value is calculated by composite interval mapping [CIM]) was detected on chromosome 3.

Thereafter, MSP_14 and MSP_16, which were polymorphisms present near the peak value, were designed as SNP markers.

The parental line was crossed with powdery mildew susceptible winter squash plants of a fixed line owned by TAKII & CO., LTD. (also referred to as "susceptible line" hereinafter)", whereby an F2 segregating population made up of 93 individuals (also referred to as "93 lines" hereinafter) was obtained.

The 93 lines were subjected to a powdery mildew fungus inoculation test. The powdery mildew fungus inoculation test was carried out in the following manner.

The powdery mildew fungus used in the test was a powdery mildew fungus (Podosphaera xanthii) derived from powdery mildew susceptible winter squash plants having developed powdery mildew spontaneously in a squash field in Konan City in Shiga Prefecture. It had been demonstrated that the powdery mildew fungus can infect the susceptible winter squash plants by the following inoculation test.

First, the powdery mildew fungus was cultured on a winter squash plant ("Ebisu", TAKII & CO., LTD.) grown in an isolated greenhouse. Fungal floras of the powdery mildew fungus on leaves of the winter squash plant were scraped from the leaves to collect conidia of the powdery mildew fungus. Thereafter, a conidial suspension was prepared by diluting the collected conidia with sterile water so as to adjust the concentration of the conidia to $1.0 \times 10^4$ conidia/ml. The thus-obtained conidial suspension was used for inoculation. Winter squash plants subjected to the inoculation were seedlings with two true leaves being expanded. 2 ml of the conidial suspension was sprayed uniformly onto the whole strain of each individual of the winter squash plants using a hand spray. Thereafter, the winter squash plants were grown for 14 days in a greenhouse at 15° C. to 25° C. and humidity of 60% to 80% under natural light.

Then, regarding the grown winter squash plants, disease investigation was carried out in the following manner.

Figure 2:
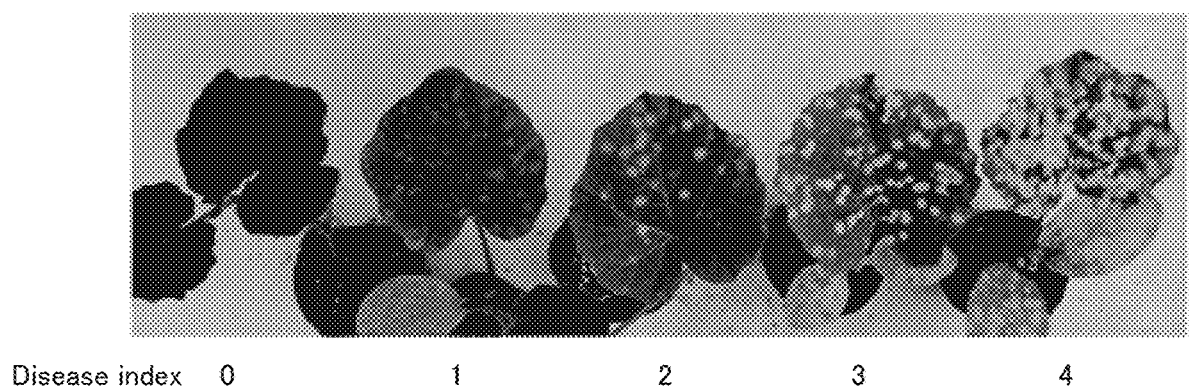
FIG. 2 is a photograph showing the criteria for evaluating the disease index of winter squash plants in Example 1.

In the disease investigation, the disease index was evaluated in accordance with the following criteria. As the evaluation criteria for the disease index, the photograph of FIG. 2 shows representative examples of individuals with disease indices of 0 to 4. In FIG. 2, regions where sporulation occurred are seen white.

Disease index 0: no symptoms are observed
Disease index 1: unclear sporulation is observed at a few spots in the inoculated leaves (not more than 5% of the area of upper surfaces of the inoculated leaves)
Disease index 2: clear sporulation is observed in limited regions (more than 5% and not more than 25% of the area of upper surfaces of the inoculated leaves)
Disease index 3: clear sporulation is observed at several spots in the inoculated leaves (more than 25% and not more than 50% of the area of upper surfaces of the inoculated leaves)
Disease index 4: clear sporulation is observed, and the inoculated leaves are mostly covered with spores (more than 50% of the area of upper surfaces of the inoculated leaves)

Then, the disease indices of the respective individuals were investigated in accordance with the above-described criteria, and the severity of the powdery mildew of each line was determined according to the following equation.

$$\text{Severity } (N) = [(0 \times n_0) + (1 \times n_1) + (2 \times n_2) + (3 \times n_3) + (4 \times n_4)] / \text{the number of the investigated individuals}$$

In the above equation, "0, 1, 2, 3, and 4" each indicate the disease index, and "$n_0$, $n_1$, $n_2$, $n_3$, and $n_4$" indicate the number of individuals evaluated as having a disease index of 0, a disease index of 1, a disease index of 2, a disease index of 3, and a disease index of 4, respectively.

Furthermore, DNAs were extracted from the 93 lines, and the polymorphism of MSP_16 was analyzed.

The results obtained are shown in Table 1 below. As shown Table 1 below, the individuals carrying MSP_16 in the resistant-type homozygous form (A) or in the heterozygous form (H) exhibited a severity of lower than 2, whereas the individuals carrying MSP_16 in the susceptible-type homozygous form exhibited a severity of 2 or higher. From these results, it was found that the resistant winter squash plants of the present invention are effective against the powdery mildew fungus. Furthermore, from the relationship between the disease indices of the 93 lines and the frequencies of appearance of the individuals having the corresponding disease indices, it was found that the mode of inheritance of the powdery mildew resistance of the parental line was monogenic incomplete dominant. Still further, it was found out that MSP_16 can be used as a marker for the powdery mildew resistance locus on chromosome 3.

TABLE 1

| Genotype (MSP_16) | Disease index | | | | | Severity |
|---|---|---|---|---|---|---|
| | 0 | 1 | 2 | 3 | 4 | |
| Resistant homo (A) | 9 | 6 | 0 | 0 | 0 | 0.4 |
| Hetero (H) | 7 | 21 | 19 | 0 | 0 | 1.3 |
| Susceptible homo (B) | 0 | 4 | 15 | 11 | 1 | 2.3 |

Example 2

Regarding novel powdery mildew resistant winter squash plants, novel powdery mildew resistance loci were identified.

The parental line was crossed with the susceptible line to obtain a backcross progeny BC1 line. The BC1 line was further backcrossed with the susceptible winter squash plant three times to obtain a BC4 line. From each backcross progeny, winter squash plants including MSP_16 and MSP_14 in the heterozygous form were selected.

MSP_17500, MSP_8, and MSP_41353, which were polymorphisms present near the peak value of QTL in Example 1, were newly designed as SNP markers. Then, regarding the 93 lines and BC4 line, polymorphic bases corresponding to MSP_16, MSP_17500, MSP_8, MSP_41353, and MSP_14 were identified. As a result, from the difference in the polymorphisms of the SNP markers between the 93 lines and the BC4 line, it was found that the distance between MSP_16 and MSP_14 on chromosome 3 was 1.6 cM.

Next, from the 93 lines and the BC4 line, 6 individuals (also referred to as "6 lines" hereinafter) different from one another in the genotypes of the SNP markers were selected. Thereafter, the 6 lines were self-crossed to produce selfed progenies. Then, regarding the selfed progenies, the inoculation test was performed in the same manner as in Example 1. The results obtained are shown in Table 2 below. In Table 2 below, "A" indicates that the SNP marker was carried in the resistant-type homozygous form, "H" indicates that the SNP marker was carried in the heterozygous form, and "B" indicates that the SNP marker was carried in the susceptible-type homozygous form. As can be seen in Table 2 below, from the individuals carrying MSP_17500, MSP_8, and MSP_41353 in the resistant-type homozygous form (A) or in the heterozygous form (H), individuals exhibiting powdery mildew resistance were obtained in the selfed progenies. From these results, it was found that, among the SNP markers, MSP_17500, MSP_8, and MSP_41353 are highly correlated with the powdery mildew resistance. Also, it was found that, because MSP_17500, MSP_8, and MSP_41353 are highly correlated with the powdery mildew resistance, a region between the sites of MSP_16 and MSP_14, which is a region including the above SNP markers, shows high correlation with the powdery mildew resistance.

The BC4 line was further backcrossed twice with the susceptible line to obtain a BC6 line. From the respective backcross progenies, winter squash plants including MSP_41353 in the heterozygous form were selected. Next, the BC6 line was self-crossed to produce a selfed progeny BC6F1 line. The BC6F1 line was self-crossed two more times in the same manner to obtain a selfed progeny BC6F3 line. Regarding the BC6F3 line, winter squash plants including MSP_41353 in the resistance-type homozygous form were selected (selected BC6F3 line). The selected BC6F3 line was deposited under Accession No. FERM BP-22336. Hereinafter, the selected BC6F3 line also is referred to as a "deposited line".

Next, regarding the respective winter squash plants (n=5), including the deposited line, shown in Table 3 below, the severity was calculated in the same manner as in Example 1. Also, regarding the respective winter squash plants including the deposited line, polymorphic bases corresponding to MSP_16, MSP_17500, MSP_8, MSP_41353, and MSP_14 were identified. The results obtained are shown in Table 3 below. In Table 3 below, "A" indicates that the SNP marker was carried in the resistance-type homozygous form, and "B" indicates that the SNP marker was carried in the susceptible-type homozygous form. As shown in Table 3 below, the deposited line was resistant to powdery mildew and carried all the SNP markers, namely, MSP_16, MSP_17500, MSP_8, MSP_41353, and MSP_14, in the resistance-type homozygous form. In contrast, the winter squash plants other than the deposited line were susceptible to powdery mildew and carried all the SNP markers, namely, MSP_16, MSP_17500, MSP_8, MSP_41353, and MSP_14, in the susceptible-type homozygous form. Moreover, the severity of the deposited line was considerably lower than those of PI 135370, PI 137866, PI 165027, PI 166046, PI 458673, and PI 458675, which are known as powdery mildew resistant winter squash plants. This reveals that the deposited line has a novel resistance locus that is different

TABLE 2

| | SNP marker | | | | Phenotype of |
| | MSP_16 | MSP_17500 | MSP_8 | MSP_41353 | MSP_14 | selfed progeny |
|---|---|---|---|---|---|---|
| Line 1 | A | A | A | A | A | resistant |
| Line 2 | H | H | H | H | A | resistant/susceptible |
| Line 3 | H | H | H | H | B | resistant/susceptible |
| Line 4 | B | B | B | B | H | susceptible |
| Line 5 | H | B | B | B | B | susceptible |
| Line 6 | B | B | B | B | B | susceptible | resistant: only resistant winter squash plants were present
resistant/susceptible: both resistant winter squash plants and susceptible winter squash plants were present
susceptible: only susceptible winter squash plants were present Example 3

Regarding a resistance locus in a novel powdery mildew resistant winter squash plant, the present example examined whether other winter squash plants do not carry this resistance locus.

from those carried by these cultivars. From these results, it was found that the resistance locus carried by the powdery mildew resistant winter squash plant according to the present invention is a novel resistance locus and that the resistance locus can be identified by MSP_17500, MSP_8, and MSP_41353.

TABLE 3

| Selling source | Cultivar name | Severity | MSP_16 | MSP_17500 | MSP_8 | MSP_41353 | MSP_14 |
|---|---|---|---|---|---|---|---|
| — | Deposited line | 1.2 | A | A | A | A | A |
| TAKII | EBISU | 4 | B | B | B | B | B |

TABLE 3-continued

| Selling source | Cultivar name | Severity | MSP_16 | MSP_17500 | MSP_8 | MSP_41353 | MSP_14 |
|---|---|---|---|---|---|---|---|
| NANTO | KOFUKI | 3.4 | B | B | B | B | B |
| MIKADO | KURIYUTAKA | 3.8 | B | B | B | B | B |
| MIKADO | Silver Cutie | 4 | B | B | B | B | B |
| MIKADO | Orange Cutie | 4 | B | B | B | B | B |
| WATANABE | Dark Horse | 4 | B | B | B | B | B |
| TOKITA | KURI SHOGUN | 3.6 | B | B | B | B | B |
| KANEKO | KUJUKURI | 4 | B | B | B | B | B |
| ENKEN | ET | 4 | B | B | B | B | B |
| ENKEN | Kent | 4 | B | B | B | B | B |
| ENKEN | BENIKURI | 4 | B | B | B | B | B |
| INFRC | KANRI 2 | 4 | B | B | B | B | B |
| INFRC | TENGUBANA | 4 | B | B | B | B | B |
| USDA | PI 135370 | 3.3 | B | B | B | B | B |
| USDA | PI 137866 | 3 | B | B | B | B | B |
| USDA | PI 165027 | 4 | B | B | B | B | B |
| USDA | PI 166046 | 3.4 | B | B | B | B | B |
| USDA | PI 458673 | 3.2 | B | B | B | B | B |
| USDA | PI 458675 | 3.8 | B | B | B | B | B |
| USDA | PI 481626 | 3.8 | B | B | B | B | B |
| USDA | PI 458683 | 4 | B | B | B | B | B |
| USDA | PI 368567 | 2.4 | B | B | B | B | B |

TAKII: TAKII & CO., LTD.
NANTO: NANTO SEED CO., LTD.
MIKADO: MIKADO KYOWA SEED CO. LTD.
WATANABE: WATANABE SEED CO., LTD.
TOKITA: TOKITA SEED CO., LTD.
KANEKO: KANEKO SEEDS CO., LTD.
ENKEN: Institute for Horticultural Plant Breeding
INFRC: International Nature Farming Research Center
USDA: United State Department of Agriculture Next, regarding the respective winter squash plants, including the deposited line, shown in Table 4 below, polymorphic bases corresponding to MSP_16, MSP_17500, MSP_8, MSP_41353, and MSP_14 were identified. The respective winter squash plants other than the deposited line are known to be susceptible to powdery mildew. In Table 4 below, "A" indicates that the SNP marker was carried in the resistance-type homozygous form, and "B" indicates that the SNP marker was carried in the susceptible-type homozygous form. As shown in Table 4 below, the deposited line carried all the SNP markers, namely, MSP_16, MSP_17500, MSP_8, MSP_41353, and MSP_14, in the resistance-type homozygous form. In contrast, the winter squash plants other than the deposited line carried all the SNP markers, namely, MSP_16, MSP_17500, MSP_8, MSP_41353, and MSP_14, in the susceptible-type homozygous form. From these results, it was found that the resistance locus can be identified by MSP_17500, MSP_8, and MSP_41353.

TABLE 4A

| Selling source | Cultivar name | MSP_16 | MSP_17500 | MSP_8 | MSP_41353 | MSP_14 |
|---|---|---|---|---|---|---|
| — | Deposited line | A | A | A | A | A |
| TAKII | HOKKORI URARA | B | B | B | B | B |
| TAKII | HOKKORI 133 | B | B | B | B | B |
| TAKII | HOKKORI HIME | B | B | B | B | B |
| TAKII | HOKKORI EBISU | B | B | B | B | B |
| TAKII | KURI EBISU | B | B | B | B | B |
| TAKII | YUMEMI | B | B | B | B | B |
| TAKII | RORON | B | B | B | B | B |
| TAKII | TSURUNASHI YAKKO | B | B | B | B | B |
| MIKADO | AJISOTA | B | B | B | B | B |
| MIKADO | AJIHEI DX | B | B | B | B | B |
| MIKADO | Cutie | B | B | B | B | B |
| MIKADO | KURANO TAKUMI | B | B | B | B | B |
| MIKADO | KURIYUTAKA 7 | B | B | B | B | B |
| MIKADO | AJIHEI | B | B | B | B | B |
| MIKADO | AJIOH | B | B | B | B | B |
| MIKADO | KURIJIMAN | B | B | B | B | B |
| TOKITA | KURITAISHOU | B | B | B | B | B |
| NANTO | TOKUNO KOFUKI | B | B | B | B | B |
| SAKATA | KURIHIRO | B | B | B | B | B |
| SAKATA | MIYAKO | B | B | B | B | B |
| SAKATA | MERUHEN | B | B | B | B | B |
| SAKATA | YUKIGESHOU | B | B | B | B | B |

SAKATA: SAKATA SEED CORPORATION

TABLE 4B

| Selling source | Cultivar name | MSP_16 | MSP_17500 | MSP_8 | MSP_41353 | MSP_14 |
|---|---|---|---|---|---|---|
| SAKATA | AKAZUKIN | B | B | B | B | B |
| SAKATA | KURIHOMARE | B | B | B | B | B |
| SAKATA | KURIBO | B | B | B | B | B |
| KANDA | Black Sea | B | B | B | B | B |
| KANDA | JINJYU | B | B | B | B | B |
| ASAHI | Primera 115 | B | B | B | B | B |
| WATANABE | HAKUSHAKU | B | B | B | B | B |
| WATANABE | KOUSHAKU | B | B | B | B | B |
| WATANABE | HOTTOKE KURITAN | B | B | B | B | B |
| WATANABE | JeJeJ | B | B | B | B | B |
| KANEKO | KURIGORO | B | B | B | B | B |

KANDA: KANDA SEED CO., LTD.
ASAHI: ASAHI INDUSTRIES CO., LTD.

Although the present invention has been described above with reference to embodiments and examples, the present invention is by no means limited to these embodiments and examples. Various changes and modifications that may become apparent to those skilled in the art may be made in the configuration and specifics of the present invention without departing from the scope of the present invention.

This application claims priority from Japanese Patent Application No. 2017-147647 filed on Jul. 31, 2017. The entire disclosure of this Japanese patent application is incorporated herein by reference.

INDUSTRIAL APPLICABILITY

As specifically described above, the powdery mildew resistance marker for winter squash plants according to the present invention enables easy screening of a powdery mildew resistant winter squash plant, for example. Also, the powdery mildew resistant winter squash plant according to the present invention includes the powdery mildew resistance locus, for example, and thus can exhibit powdery mildew resistance, for example. Accordingly, the powdery mildew resistant winter squash plant of the present invention can eliminate the necessity of prevention and extermination of powdery mildew using agricultural chemicals as performed conventionally, whereby problems of labor and cost for spraying the agricultural chemicals can be avoided, for example. Therefore, the present invention is very useful in the field of agriculture such as breeding, for example.

SEQUENCE LISTING

TF17063WO_ST25.txt

The invention claimed is:

1. A powdery mildew resistant winter squash plant comprising:
   a powdery mildew resistance locus on chromosome 3,
   wherein the powdery mildew resistance locus comprises at least one SNP marker selected from the group consisting of MSP 17500, MSP 8, and MSP 41353, and the powdery mildew resistance locus maps to a position between two SNP markers MSP_14 and MSP_16,
   wherein the powdery mildew resistant winter squash plant is *Cucurbita maxima* plant, and the *Cucurbita maxima* plant is not a hybrid with *Cucurbita pepo* plant.

2. The powdery mildew resistant winter squash plant according to claim 1, wherein
   the powdery mildew resistance locus comprises at least one polynucleotide selected from the group consisting of the following polynucleotides (a), (b), and (c):
   (a) the following polynucleotide (a1) or (a3):
      (a1) a polynucleotide consisting of a sequence of SEQ ID NO: 1,
      (a3) a polynucleotide that consists of a sequence having at least 95% sequence identity to the base sequence of the polynucleotide (a1) with a 37th base (C) in the sequence of the polynucleotide (a1) being conserved,
   (b) the following polynucleotide (b1) or (b3):
      (b1) a polynucleotide consisting of a sequence of SEQ ID NO: 2,
      (b3) a polynucleotide that consists of a sequence having at least 95% sequence identity to the base sequence of the polynucleotide (b1) with a 59th base (T) in the sequence of the polynucleotide (b1) being conserved, and
   (c) the following polynucleotide (c1) or (c3):
      (c1) a polynucleotide consisting of a sequence of SEQ ID NO: 3,
      (c3) a polynucleotide that consists of a sequence having at least 95% sequence identity to the base sequence of the polynucleotide (c1) with a 34th base (C) in the sequence of the polynucleotide (c1) being conserved.

3. The powdery mildew resistant winter squash plant according to claim 1, wherein
   the powdery mildew resistance locus maps to a position between two SNP markers selected from the group consisting of MSP_17500, MSP_8, and MSP_41353 on the chromosome.

4. The powdery mildew resistant winter squash plant according to claim 1, wherein
   the powdery mildew resistant winter squash plant is a winter squash plant having been deposited under Accession No. FERM BP-22336 or a progeny line thereof,
   wherein the progeny line comprises the powdery mildew resistance locus.

5. The powdery mildew resistant winter squash plant according to claim 1, wherein
   the powdery mildew resistant winter squash plant is a plant body or a part thereof.

6. The powdery mildew resistant winter squash plant according to claim 1, wherein
   the powdery mildew resistant winter squash plant is a seed.

7. The powdery mildew resistant winter squash plant according to claim 1, wherein
   the winter squash plant is a cultivar of a winter squash plant.

8. A method for producing a winter squash plant, the method comprising:
   detecting, in one or more winter squash plants to be examined, at least one SNP marker selected from the group consisting of MSP_17500, MSP_8, and MSP_41353 to identify a powdery mildew resistant winter squash plant on chromosome 3; and
   crossing the powdery mildew resistant winter squash plant with another winter squash plant to produce a progeny winter squash plant; wherein
   the progeny winter squash plant comprises the powdery mildew resistant winter squash plant comprising the powdery mildew resistance locus on chromosome 3, wherein
   the powdery mildew resistance locus comprises at least one SNP marker selected from the group consisting of MSP_17500, MSP_8, and MSP_41353, and the powdery mildew resistance locus maps to a position between two SNP markers MSP_14 and MSP_16,
   wherein the powdery mildew resistant winter squash plant is *Cucurbita maxima* plant, and the *Cucurbita maxima* plant is not a hybrid with *Cucurbita pepo* plant.

9. The production method according to claim 8, wherein the detecting comprises detecting at least one polynucleotide selected from the group consisting of the following polynucleotides (a), (b), and (c):
(a) the following polynucleotide (a1) or (a3):
(a1) a polynucleotide consisting of a sequence of SEQ ID NO: 1,
(a3) a polynucleotide that consists of a sequence having at least 95% sequence identity to the sequence of the polynucleotide (a1) with a 37th base (C) in the sequence of the polynucleotide (a1) being conserved,
(b) the following polynucleotide (b1) or (b3):
(b1) a polynucleotide consisting of a sequence of SEQ ID NO: 2,
(b3) a polynucleotide that consists of a sequence having at least 95% sequence identity to the sequence of the polynucleotide (b1) with a 59th base (T) in the sequence of the polynucleotide (b1) being conserved, and
(c) the following polynucleotide (c1) or (c3):
(c1) a polynucleotide consisting of a sequence of SEQ ID NO: 3,
(c3) a polynucleotide that consists of a sequence having at least 95% sequence identity to the sequence of the polynucleotide (c1) with a 34th base (C) in the sequence of the polynucleotide (c1) being conserved.

10. The production method according to claim 8, wherein the detecting comprises the detecting the powdery mildew resistance locus that maps to a position between two SNP markers selected from the group consisting of MSP_17500, MSP_8, and MSP_41353 on the chromosome.

11. The production method according to claim 8, further comprising the following step (b):
(b) selecting a powdery mildew resistant winter squash plant from one or more winter squash plants obtained in the step (a) or one or more progeny lines thereof.

12. The production method according to claim 11, wherein
the selection in the step (b) is selection of the powdery mildew resistant winter squash plant comprising a powdery mildew resistance locus on chromosome 3.

13. The production method according to claim 11, wherein
the selection in the step (b) is selection of the powdery mildew resistant winter squash plant comprising a powdery mildew resistance locus comprising at least one SNP marker selected from the group consisting of MSP_17500, MSP_8, and MSP_41353.

14. The production method according to claim 11, wherein
the selection in the step (b) is selection of the powdery mildew resistant winter squash plant comprising a powdery mildew resistance locus comprising at least one polynucleotide selected from the group consisting of the following polynucleotides (a), (b), and (c):
(a) the following polynucleotide (a1) or (a3):
(a1) a polynucleotide consisting of a sequence of SEQ ID NO: 1,
(a3) a polynucleotide that consists of a sequence having at least 95% sequence identity to the sequence of the polynucleotide (a1) with a 37th base (C) in the sequence of the polynucleotide (a1) being conserved,
(b) the following polynucleotide (b1) or (b3):
(b1) a polynucleotide consisting of a sequence of SEQ ID NO: 2,
(b3) a polynucleotide that consists of a sequence having at least 95% sequence identity to the sequence of the polynucleotide (b1) with a 59th base (T) in the sequence of the polynucleotide (b1) being conserved, and
(c) the following polynucleotide (c1) or (c3):
(c1) a polynucleotide consisting of a sequence of SEQ ID NO: 3,
(c3) a polynucleotide that consists of a sequence having at least 95% sequence identity to the sequence of the polynucleotide (c1) with a 34th base (C) in the sequence of the polynucleotide (c1) being conserved.

15. The production method according to claim 11, wherein
the selection in the step (b) is selection of the powdery mildew resistant winter squash plant comprising a powdery mildew resistance locus that maps to a position between two SNP markers selected from the group consisting of MSP_16, MSP_17500, MSP_8, MSP_41353, and MSP_14 on the chromosome.

16. The production method according to claim 8, wherein
the powdery mildew resistant winter squash plant is a winter squash plant deposited with the International Patent Organism Depositary National Institute of Technology and Evaluation under Accession No. FERM BP-22336 or a progeny line thereof,
wherein the progeny line comprises the powdery mildew resistance locus.

17. The powdery mildew resistant winter squash plant according to claim 1, wherein
the powdery mildew resistance locus comprises MSP 17500, MSP 8, and MSP 41353.

18. The production method according to claim 8, wherein the detecting comprises detecting MSP 17500, MSP 8, and MSP 41353.

19. The powdery mildew resistant winter squash plant according to claim 1, wherein the *Cucurbita maxima* plant is not a hybrid with a related species.

20. The production method according to claim 8, wherein the *Cucurbita maxima* plant is not a hybrid with a related species.

* * * * *

```
SEQUENCE LISTING

<160> NUMBER OF SEQ ID NOS: 5

<210> SEQ ID NO 1
<211> LENGTH: 94
<212> TYPE: DNA
<213> ORGANISM: Cucurbita maxima

<400> SEQUENCE: 1
cttcatattg ttttgtggta caccataagc caagtacgcc tttcagaaaa caaagtagat    60
attatagcct gactgtctat gaagaactaa aaag                                94

<210> SEQ ID NO 2
<211> LENGTH: 88
<212> TYPE: DNA
<213> ORGANISM: Cucurbita maxima

<400> SEQUENCE: 2
acatctgaaa aagttgaagc tgttatgtga tggagagatt gcagagtggt tgaaaacgtt    60
tgctccccac cttgccaaac aggtcaaa                                      88

<210> SEQ ID NO 3
<211> LENGTH: 67
<212> TYPE: DNA
<213> ORGANISM: Cucurbita maxima

<400> SEQUENCE: 3
gagagtgggc aacaatttcc ccttgaagaa gagctcgtcg gcggcggtca ttgtgtgatt    60
actggga                                                             67
```

```
<210> SEQ ID NO 4
<211> LENGTH: 73
<212> TYPE: DNA
<213> ORGANISM: Cucurbita maxima

<400> SEQUENCE: 4
atgaggaatg attacgtttg gaaactttgc aggttgtggg agtgctggtt ggcaagcccc      60
tgaacaactt ctt                                                         73

<210> SEQ ID NO 5
<211> LENGTH: 120
<212> TYPE: DNA
<213> ORGANISM: Cucurbita maxima

<400> SEQUENCE: 5
attgtcacta gaatttggcc aaacactaag tacctggatg tgattgtgac cggagccatg      60
gctcagtaca tacccacctt ggaactttac agtggagggt tacccatggc ttgcactatg     120
```